(12) United States Patent
Mandrusov et al.

(10) Patent No.: US 7,901,359 B2
(45) Date of Patent: *Mar. 8, 2011

(54) ULTRASOUND ENERGY DRIVEN INTRAVENTRICULAR CATHETER TO TREAT ISCHEMIA

(75) Inventors: Evgenia Mandrusov, Campbell, CA (US); Jeffrey Steward, Lakewood, CO (US); Marshall Sherman, Cardiff-by-the-Sea, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 749 days.

This patent is subject to a terminal disclaimer.

(21) Appl. No.: 11/296,595

(22) Filed: Dec. 6, 2005

(65) Prior Publication Data

US 2006/0100554 A1  May 11, 2006

Related U.S. Application Data (63) Continuation of application No. 10/817,358, filed on Apr. 1, 2004, now Pat. No. 7,001,336, which is a continuation of application No. 09/774,334, filed on Jan. 30, 2001, now Pat. No. 6,740,040.

(51) Int. Cl.
*A61B 17/00* (2006.01)
(52) U.S. Cl. .............. 600/459; 604/22; 601/2
(58) Field of Classification Search ............ 601/2; 604/22, 113, 117, 118, 523; 606/11, 15, 606/31, 32, 41, 159; 600/439, 466
See application file for complete search history.

(56) References Cited

U.S. PATENT DOCUMENTS

| | | | |
|---|---|---|---|
| 5,279,546 A | 1/1994 | Mische et al. |
| 5,295,484 A | 3/1994 | Marcus et al. |
| 5,342,292 A | 8/1994 | Nita et al. |
| 5,596,995 A | 1/1997 | Sherman et al. |
| 5,606,974 A | 3/1997 | Castellano et al. |
| 5,630,837 A | 5/1997 | Crowley |
| 5,725,494 A | 3/1998 | Brisken |
| 5,725,523 A | 3/1998 | Mueller |
| 5,735,280 A | 4/1998 | Sherman et al. |

(Continued)

OTHER PUBLICATIONS

Hyuck Moon Kwon et al., "Percutaneous Transmyocardial Revascularization Induces Angiogenesis: A Histologic and 3-Dimensional Micro Computed Tomography Study", J. Korean Med. Sci. 1999, (The Korean Academy of Med. Scien.) pp. 502-510.

(Continued)

*Primary Examiner* — Brian Casler
*Assistant Examiner* — Parikha S Mehta
(74) *Attorney, Agent, or Firm* — Squire, Sanders & Dempsey (US) LLP (57) ABSTRACT

A method and apparatus for improving blood flow to an ischemic region (e.g., myocardial ischemia) a patient is provided. An ultrasonic transducer is positioned proximate to the ischemic region. Ultrasonic energy is applied at a frequency at or above 1 MHz to create one or more thermal lesions in the ischemic region of the myocardium. The thermal lesions can have a gradient of sizes. The ultrasound transducer can have a curved shape so that ultrasound energy emitted by the transducer converges to a site within the myocardium, to create a thermal lesion without injuring the epicardium or endocardium.

23 Claims, 8 Drawing Sheets

U.S. PATENT DOCUMENTS

| | | |
|---|---|---|
| 5,735,811 A | 4/1998 | Brisken |
| 5,824,005 A | 10/1998 | Motamedi et al. |
| 5,827,203 A | 10/1998 | Nita |
| 5,846,218 A | 12/1998 | Brisken et al. |
| 5,857,997 A | 1/1999 | Cimino et al. |
| 5,860,951 A | 1/1999 | Eggers et al. |
| 5,873,855 A | 2/1999 | Eggers et al. |
| 5,888,198 A | 3/1999 | Eggers et al. |
| 5,891,095 A | 4/1999 | Eggers et al. |
| 5,910,154 A | 6/1999 | Tsugita et al. |
| 5,911,734 A | 6/1999 | Tsugita et al. |
| 5,916,214 A | 6/1999 | Cosio et al. |
| 5,944,716 A | 8/1999 | Hektner |
| 5,971,980 A | 10/1999 | Sherman |
| 5,989,208 A | 11/1999 | Nita |
| 5,989,274 A | 11/1999 | Davison et al. |
| 5,993,443 A | 11/1999 | Murphy-Chutorian et al. |
| 6,001,091 A | 12/1999 | Murphy-Chutorian et al. |
| 6,004,269 A | 12/1999 | Crowley et al. |
| 6,007,514 A | 12/1999 | Nita |
| 6,010,476 A | 1/2000 | Saadat |
| 6,027,497 A | 2/2000 | Daniel et al. |
| 6,027,520 A | 2/2000 | Tsugita et al. |
| 6,030,380 A | 2/2000 | Auth et al. |
| 6,032,674 A | 3/2000 | Eggers et al. |
| 6,036,685 A | 3/2000 | Mueller |
| 6,042,581 A | 3/2000 | Ryan et al. |
| 6,042,598 A | 3/2000 | Tsugita et al. |
| 6,045,565 A | 4/2000 | Ellis et al. |
| 6,056,742 A | 5/2000 | Murphy-Chutorian et al. |
| 6,059,770 A | 5/2000 | Peacock, III et al. |
| 6,068,638 A | 5/2000 | Makower |
| 6,074,384 A | 6/2000 | Brinkmann et al. |
| 6,165,200 A | 12/2000 | Tsugita et al. |
| 6,270,513 B1 | 8/2001 | Tsugita et al. |
| 6,283,935 B1 | 9/2001 | Laufer et al. |
| 6,312,402 B1 * | 11/2001 | Hansmann .................. 604/22 |
| 6,371,969 B1 | 4/2002 | Tsugita et al. |
| 6,575,956 B1 * | 6/2003 | Brisken et al. .............. 604/500 |
| 6,645,147 B1 * | 11/2003 | Jackson et al. .............. 600/458 |
| 2002/0049395 A1 * | 4/2002 | Thompson et al. ............. 601/2 |

OTHER PUBLICATIONS

Boston Scientific Corp. Press Release, "Boston Sci. Announces First Human Use of RF-PMR Technology to Treat Advanced Coronary Artery Disease", Natick, Mass. Feb. 9, 2000, 3 pgs.

O.H. Frazier et al., "Transmyocardial Revascularization with a Carbon Dioxide Laser in Patients with End-Stage Coronary Artery Disease", The New England J. of Med., vol. 341, No. 14, Sep. 30, 1999, 2 pgs.

* cited by examiner

ULTRASOUND ENERGY DRIVEN INTRAVENTRICULAR CATHETER TO TREAT ISCHEMIA

CROSS REFERENCE

This application is a continuation of of U.S. patent application Ser. No. 10/817,358, now U.S. Pat. No. 7,001,336 filed on Apr. 1, 2004, which is a continuation of U.S. patent application Ser. No. 09/774,334, now U.S. Pat. No. 6,740,040 filed on Jan. 30, 2001.

BACKGROUND

1. Field of the Invention

The invention relates generally to treatment of heart disease. More particularly, the invention is directed to an ultrasonic method and apparatus to treat ischemic tissue.

2. Description of the Background

Heart disease is a significant health problem and impairs the quality of life for millions of people. A common form of heart disease is ischemic heart disease, a condition in which parts of the heart muscle, or myocardium, do not receive an adequate supply of blood. Typically, this condition occurs when the arteries that carry blood to the myocardium become clogged by plaque build-up on their inner walls. The clogged arteries hinder blood flow, and the myocardium is deprived of oxygen and other nutrients. Ischemia results.

A number of methods are employed to improve blood flow to myocardium downstream of an arterial blockage. Many of these methods, such as coronary bypass surgery and balloon angioplasty, involve circumvention or removal of the arterial obstruction to re-establish blood flow. An alternate set of methods, known as transmyocardial revascularization (TMR) or percutaneous transmyocardial revascularization (PMR), involve the creation of small channels in the myocardium itself to reperfuse the ischemic tissue.

Channels created by the TMR or PMR procedures were initially believed to relieve ischemia by allowing blood to flow directly from the ventricle into the ischemic myocardium. More recent studies suggest that the channels do not remain open. Instead, the TMR or PM procedures may stimulate angiogenesis, the creation of new blood vessels, and it is the new blood vessels that restore blood flow to the ischemic region. Angiogenesis is a natural response to cellular damage and results when injured cells alert the body to heal itself. It is believed that cells damaged by the TMR or PMR procedures produce and excrete special chemicals, such as cytokines and growth factors, which signal surrounding cells to initiate the formation of new blood vessels. The new blood vessels grow into the ischemic region, supplying the region with blood.

TMR and PMR methods used to create channels in the myocardium include mechanical coring, ultrasonic cutting, laser drilling, and using radio frequency (RF) energy to burn through the heart tissue. The mechanical, ultrasonic, laser, or RF device is typically positioned at the end of a catheter. The catheter is inserted either through the patient's cardiovascular system to place the device into the inside of the heart or through a small cavity in the patient's chest to place the device onto the outside of the heart.

Mechanical coring methods create channels in the myocardium by displacing or removing the heart tissue. Cutting devices such as needles or blades are employed.

Ultrasonic devices, such as those described in U.S. Pat. No. 5,827,203 to Nita and U.S. Pat. No. 5,989,274 to Davison et al., are also used to mechanically scrape or cut channels into the heart tissue. With these devices, ultrasonic energy is applied at frequencies between 20 kHz and 100 kHz to a tip at the end of a catheter. The ultrasonic energy causes the tip to vibrate and pierce the surface of the heart to form a channel. A blade may be attached to the tip to facilitate cutting.

Lasers, such as $CO_2$ lasers, vaporize the heart tissue to burn channels in the myocardium. Myocardial revascularization using lasers is described, for example, in U.S. Pat. No. 6,074,384 to Brinkmann et al.

RF energy can also be used to burn holes in the myocardium, as described in U.S. Pat. No. 6,030,380 to Auth et al., U.S. Pat. No. 5,944,716 to Hektner, and U.S. Pat. No. 6,032,674 to Eggers et al.

A problem with the above procedures is that creating channels in the myocardium causes excessive trauma and damage to the heart tissue. The epicardium, endocardium, or both are punctured to form the channels, leading to a risk of complications such as hemorrhaging and scarring. The possibility that an embolus will form and cause, for instance, a stroke is another potential complication with the procedures.

As to problems with the particular methods described above, laser energy is known to kill healthy cells, which may worsen the patient's condition. The laser procedure may also cause denervation, which relieves the chest pain associated with ischemia, but permanently damages the heart muscle. In addition, controlling the location and depth of a channel formed by laser or RF energy is difficult, making accidental damage to healthy tissue more likely. RF energy is also diffuse, making it especially difficult to localize damage from the RF energy device, and creating problems such as the coagulation of surrounding blood.

U.S. Pat. No. 5,827,203 also describes using low frequency ultrasonic energy to massage the ischemic myocardium, without cutting or removing the tissue, as is required when creating channels. However, although massaging the tissue is less traumatic to the heart tissue than creating channels, massaging alone does not fully treat ischemia and does not cause the cellular damage necessary to stimulate angiogenesis.

SUMMARY

Embodiments of the present invention include methods and apparatuses for treating ischemic myocardium. The invention minimizes injury to the heart tissue and risk to the patient while still causing the cellular damage believed necessary for revascularization of ischemic tissue.

In one embodiment, an ultrasonic device is used to form localized, precisely placed thermal lesions in and near the ischemic tissue. Ultrasonic energy can be advantageously locally directed and is relatively easy to control. Therefore, the thermal lesions formed by ultrasonic energy can induce angiogenesis in myocardium without creating channels and without excessive damage and trauma to the tissue. Even beyond inducing angiogenesis, it is believed that the method will assist in increasing blood flow to the treated region and mitigates the progression and symptoms of ischemia.

In one particular embodiment, a catheter having a distal end is inserted into the patient. The catheter has at least one ultrasonic transducer on the distal end. The ultrasonic transducer is positioned proximate to the ischemic region. Ultrasonic energy is applied at a frequency at or above 1 MHz to create a first thermal lesion in the ischemic region of the myocardium. For example, the ultrasonic energy can be applied at frequencies between 4 MHz and 15 MHz to create the thermal lesion.

The method may further include repositioning the ultrasonic transducer and applying ultrasonic energy at a frequency at or above 1 MHz to create one or more second thermal lesions in the myocardium. The second thermal lesion(s) may be created in the ischemic region adjacent the first thermal lesion or in myocardium adjacent the ischemic region. The first and second lesions can be created so as to have a gradient of sizes.

An embodiment of an ultrasonic catheter within the present invention can have an array of ultrasonic transducers. Ultrasonic energy at a frequency greater than approximately 1 MHz can be applied from the ultrasonic transducers in the array to create additional thermal lesions. The ultrasonic transducers of the array may be independently coupled to a power source and independently controlled by a controller, allowing ultrasonic energy of varying power and duration to be independently applied from each transducer in the array. The controller can control the duty cycle of the power source, so that higher powers can be applied to the tissue without overheating the transducer. The independently controlled transducers in the array can advantageously be used to create multiple thermal lesions that have a gradient of sizes.

The ultrasonic transducer can have a shape that causes the ultrasonic energy emitted by the transducer to converge in a region located internal to the myocardium and at a distance from the endocardium and epicardium. The transducer can have, for example, a bowl-like, partial cylinder, or hollow hyperboloid-like shape. Accordingly, the thermal lesions produced by the converging ultrasonic energy will be located internal to the myocardium and distal from the endocardium and epicardium. This allows ischemic region internal to the myocardium to be treated without injuring the endocardium or epicardium.

These and other embodiments and aspects of the present invention will be better understood in view of the attached drawings and the following detailed description.

BRIEF DESCRIPTION OF THE FIGURES

FIGS. 3A, 3B, and 3C illustrate multiple thermal lesions in the ischemic region and myocardium adjacent the ischemic region with arrows indicating the direction of concentration gradients of growth factors and other angiogenesis stimulating substances. In FIG. 3A, the thermal lesions are approximately equivalent in size, in FIGS. 3B and 3C, the thermal lesions decrease in size from the center of the ischemic region.

DETAILED DESCRIPTION

Figure 1:
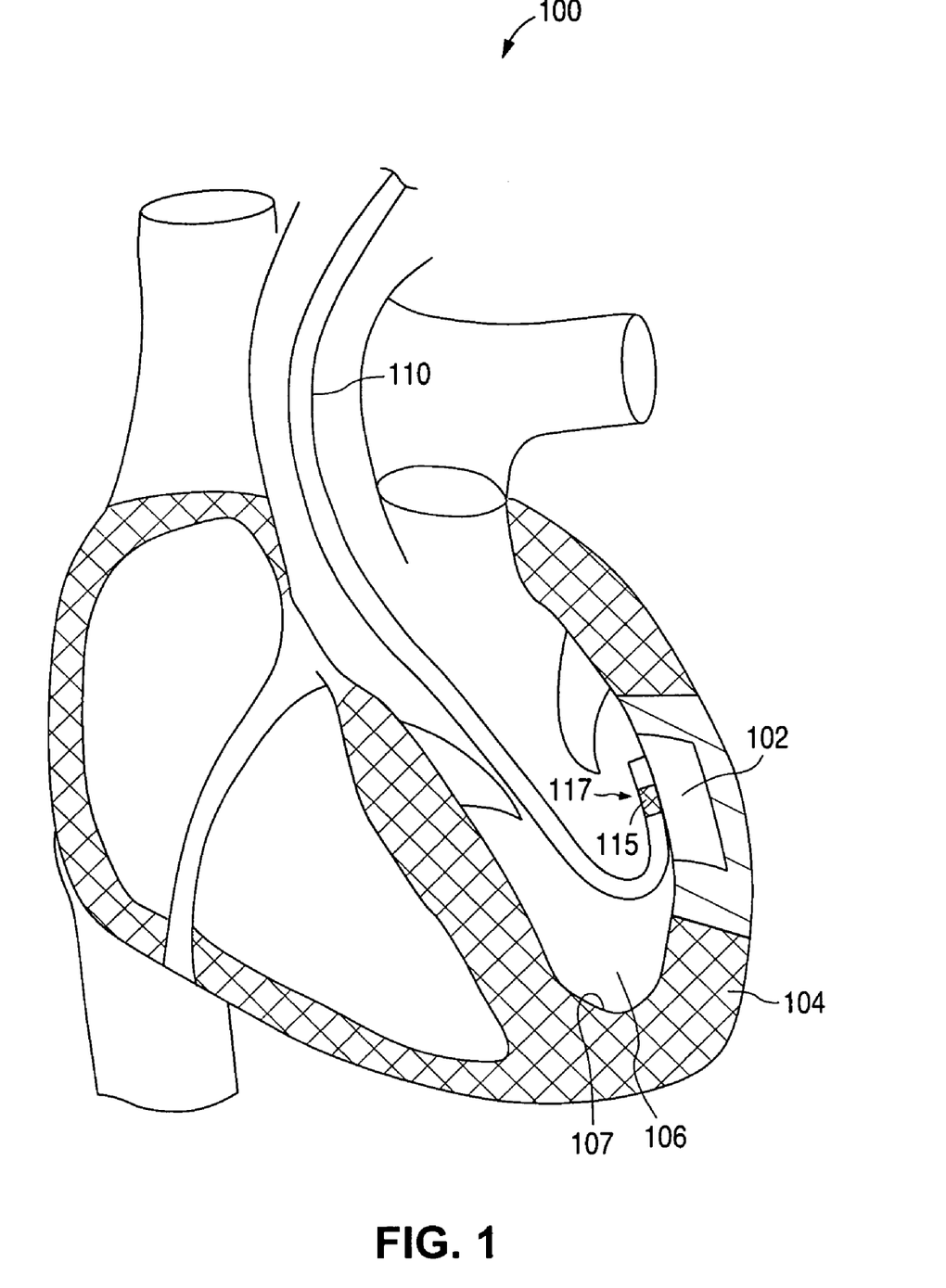
FIG. 1 is a diagrammatic view of a human heart in partial cross section showing a catheter with a distal end proximate to an ischemic region of the myocardium.

FIG. 1 illustrates a heart 100 having an ischemic region 102 in the myocardium 104 of the left ventricle 106. A catheter 110 has been inserted into the left ventricle 106. An ultrasound transducer 115 is mounted on distal portion 117 of catheter 110. Ultrasound transducer 115 is positioned adjacent to the endocardial surface 107 and proximate to ischemic region 102, where it is used to treat ischemic region 102, as described below. In particular, transducer 115 is positioned on the endocardial surface 107 laterally adjacent ischemic region 102.

Although FIG. 1 illustrates ischemic region 102 and catheter 110 in the left ventricle 106, which is particularly susceptible to ischemia, the beneficial effect of the procedures and devices described herein can be used to treat any ischemic area of the heart or other body tissue.

Figure 2A:
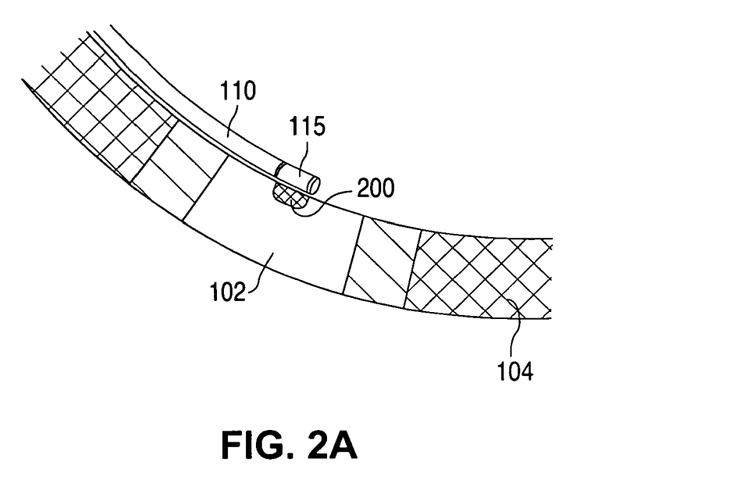
FIG. 2A illustrates a "side-fire" ultrasound transducer of a catheter that is located adjacent to an ischemic region of the myocardium, and a thermal lesion produced in the ischemic region by ultrasound energy from the transducer.

FIG. 2A illustrates a portion of myocardium 104 with an ischemic region 102. Ultrasound transducer 115 on catheter 110 is oriented toward ischemic region 102. A thermal lesion 200 has been created in ischemic region 102 by ultrasound energy that was emitted from ultrasound transducer 115 at a frequency at or above 1 MHz.

As defined herein, a "thermal lesion" is a localized injury to tissue caused by application of ultrasonic energy at frequencies at or above 1 MHz. In the various embodiments of the invention, such thermal lesions are created to treat the ischemic tissue. Ultrasonic energy delivered to tissue at frequencies at or above 1 MHz heats the tissue to cause damage to cells within the area of the lesion. It is believed that the cells damaged by the high-frequency ultrasonic energy produce angiogenesis stimulating substances such as cytokines and growth factors. The angiogenesis stimulating substances promote the growth of new blood vessels, which may grow toward, away from, and/or in the vicinity of the angiogenesis stimulating substances. Thus, the tissue in and around the thermal lesion is revascularized.

By contrast, the above-described ultrasonic references (i.e., Nita and Davison et al.) use ultrasound energy having a frequency of 20 kHz to 100 kHz to shake an end effector against the tissue, thereby producing gross mechanical motion of the tissue. The gross mechanical motion massages and shakes the tissue, but does not cause revascularization. In the embodiments of the present invention, the ultrasonic transducer sends ultrasonic energy directly into the tissue at frequencies that begin at 1 MHz, e.g. 10 MHz, at least an order of magnitude higher than the above references, to obtain molecular motion and thus cause the requisite thermal cellular damage.

Such thermal lesions can be created using, for example, the ultrasound device described in U.S. Pat. No. 5,735,280 to Sherman and Castellano, which patent is incorporated herein by reference in its entirety. In the following discussion, aspects of such a device, and modifications thereto in accordance with the present invention are discussed in detail.

Figure 2B:
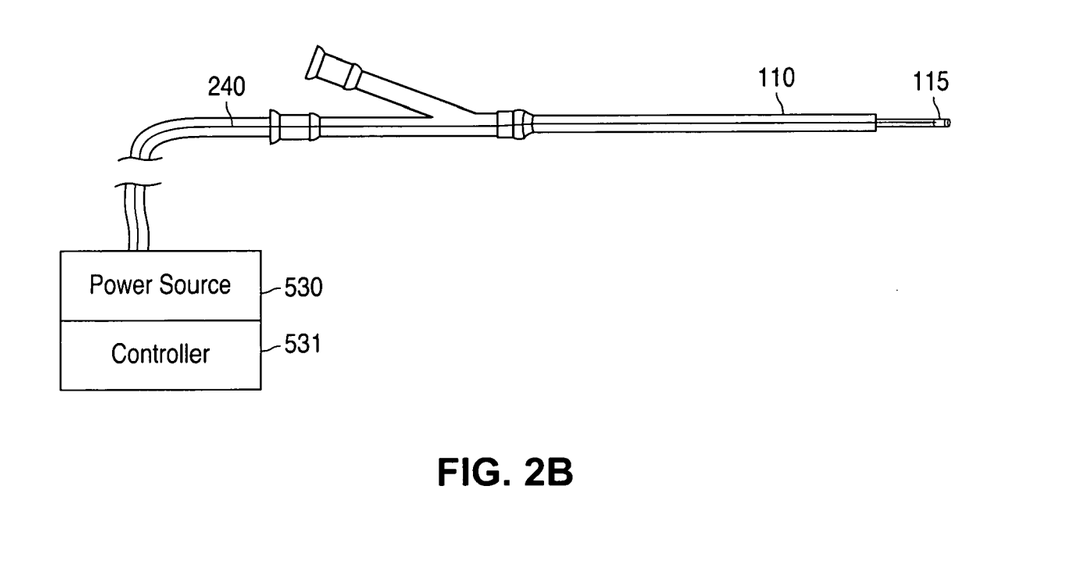
FIG. 2B is a plan view of a catheter with a transducer on the distal end. Electrical leads connect the transducer to a power supply and controller.

As illustrated in FIG. 2B, transducer 115 is connected to a power source 530 and controller 531 via electrical leads 240 that traverse the length of catheter 110. Power source 530 provides energy to transducer 115 through electrical leads 240. Controller 531 (typically containing a microprocessor) controls the power supplied to transducer 115 from power source 530. Ultrasound transducer 115 is typically a piezoelectric crystal that can deliver ultrasonic energy at frequencies greater than 1 MHz. In this embodiment, transducer 115 is a cylindrical, "side-fire" transducer. Ultrasonic energy is emitted radially from the sides of the transducer.

To create a thermal lesion, ultrasonic energy can be delivered to the tissue from transducer 115 at, for the example of a cylindrical transducer, a power of between 2 and 20 watts, typically 8-10 watts for a duration time in the range of 15 to 300 seconds, typically 120 seconds. The ultrasonic energy is delivered at a frequency at or above 1 MHz, e.g., between 1 MHz and 15 MHz, or more typically between 4 MHz and 10 MHz.

In creating the thermal lesion(s) in accordance with the present invention, it is desirable to control the temperature of the ultrasound transducer 115. In particular, it is desirable to keep the transducer from getting so hot as to boil or carbonize blood or tissue that directly contacts transducer 115. To avoid such a situation, the temperature of the transducer is kept at or below 70° C. to 80° C., as monitored by temperature sensors placed on the transducer crystal. The temperature sensors provide feedback to the controller, which accordingly adjusts the power supplied to transducer 115. The power supplied to the transducer may be controlled by appropriate setting of the voltage level. Alternatively, the duty cycle of the power source can be regulated in a manner that achieves high peak power while maintaining a relatively low effective power level, as described in U.S. Pat. No. 5,971,980 to Sherman, which is incorporated herein by reference in its entirety. Because the transducer cools more quickly than the tissue, the duty cycle can be used to keep the transducer below the desired temperature while maintaining the peak power level needed to create the thermal lesions.

Catheter 110 can be any surgical tool capable of advancing and positioning ultrasound transducer 115. For example, catheter 110 can be a flexible guide catheter having a steerable tip, such as the catheter described in U.S. Pat. No. 5,857, 997. Catheter 110 may be fitted with additional surgical equipment, such as a fiber optic scope for internal viewing, control circuitry for synchronizing delivery of ultrasound energy with the heartbeat cycle, or other devices for enhancing the safety and effectiveness of the surgical method.

Methods for accessing the heart with a surgical tool such as catheter 110 are well known. For example, catheter 110 can be inserted into the femoral artery and maneuvered through the aorta and into the left ventricle or into one of the main coronary arteries such as the left anterior descending or left circumflex. Alternatively, the heart can be externally accessed by inserting catheter 110 through an opening in the patient's chest, e.g., a sternotomy or mini-thoracotomy, and positioning the ultrasound transducer 115 adjacent the epicardial surface or pericardial sac. Fluoroscopic, ultrasound, or other imaging techniques can be used to view catheter 110 and transducer 115 as they are guided through the body and positioned proximate to ischemic region 102. The location within the body of ischemic region 102 can be identified by known techniques, such as angiography. Note also that creation of thermal lesions in accordance with the embodiments of the invention may be performed in conjunction with other procedures, for example coronary artery bypass graft (CABG) surgery.

Exemplary Treatment Regimes

As mentioned above, we believe that, by creating thermal lesions in myocardium using ultrasonic energy applied at a frequency at or above 1 MHz without cutting or piercing the tissue, the tissue will be sufficiently damaged to release angiogenesis stimulating substances. The thermal lesions do not traumatize the tissue to the degree of conventional TMR and PMR procedures. In the description below, various treatment regimes are discussed which provide thermal lesions in various locations and amounts, as may be appropriate to particular clinical situations.

A. Creating Multiple Thermal Lesions

Figure 3A:
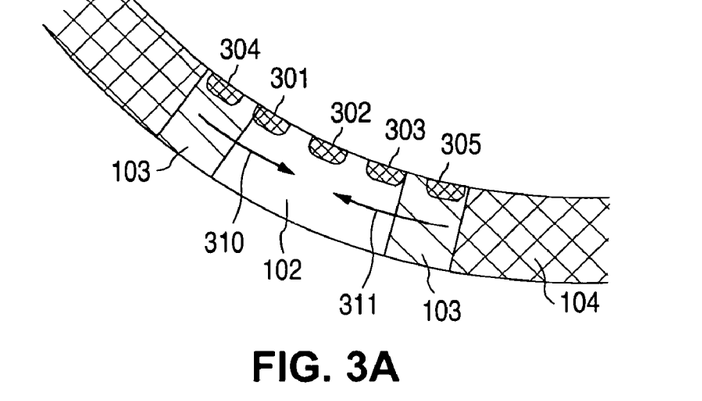

Multiple thermal lesions, as illustrated by exemplary thermal lesions 301, 302, and 303 of FIG. 3A, may be created throughout the ischemic region. We believe that the damaged cells in the thermal lesion will release angiogenesis stimulating substances, such as growth factors and cytokines, and that new blood vessels will grow in the vicinity of the substances so released. In a larger ischemic region, multiple thermal lesions throughout the ischemic region will cause angiogenesis stimulating substances to be released throughout the region, and thus promote revascularization of the entire region. The number of thermal lesions needed to treat an ischemic area depends on factors such as the size of the ischemic area and degree of ischemia, as determined by the physician, and the size of the thermal lesions produced. The size of the thermal lesion produced, in terms of the surface area of the ischemic tissue covered by the thermal lesion, generally corresponds to the size of the transducer and the amount of contact the transducer has with the tissue. Typically, transducer 115 is 1 to 10 mm long and 1 to 10 mm in width (e.g., the diameter of a cylindrical transducer), creating thermal lesions that cover a surface area 1 to 10 mm in length and 1 to 10 mm in width. Typically, at least one thermal lesion is created for each square centimeter ($cm^2$) of ischemic region.

FIG. 3A also illustrates thermal lesions 304 and 305, which may be created in region 103 adjacent the ischemic region, where the heart tissue is healthier. New blood vessels may form more readily in the healthier tissue and may grow from the healthier tissue in region 103 toward the angiogenesis stimulating substances produced by the damaged cells in thermal lesions 301, 302, and 303, as illustrated by the arrows 310 and 311.

Figure 3B:
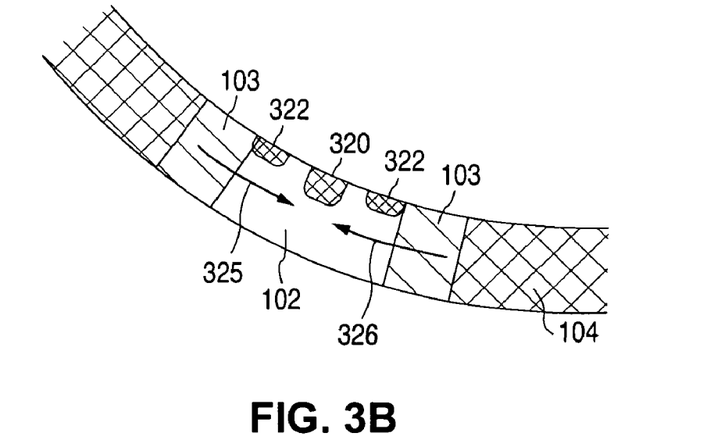

In another embodiment, illustrated by the example of FIG. 3B, the size of the thermal lesions is varied to produce a gradient of sizes of the thermal lesions. Larger thermal lesions, such as thermal lesion 320, are created towards the center of the ischemic tissue. The larger thermal lesions 320 typically release larger amounts of angiogenesis stimulating substances than do the smaller thermal lesions 322 at the edges of the ischemic region. Thus, the size gradient of thermal lesions creates a concentration gradient of the released angiogenesis stimulating substances, illustrated by arrows 325, 326. It is believed that more new blood vessels may grow in the vicinity of the higher concentrations of the angiogenesis stimulating substances or that the higher concentration may stimulate the new blood vessels to grow over a larger distance. The gradient of sizes of the thermal lesions therefore may promote growth of new blood vessels in the center of ischemic region 102.

For a given size of transducer 115, the size of a thermal lesion can be varied by varying the power output of the ultrasound transducer. The power output can be varied either by varying the voltage applied to transducer 115, the duty cycle (as described above), or the frequency of the ultrasound energy. In general, for transducer geometries such as cylindrical or flat, in which the ultrasound energy that radiates from the transducer does not converge (see below), more power creates a deeper lesion. The distance the transducer is from the myocardial tissue will also determine how deep into the tissue the ultrasonic energy penetrates and, hence, the size of the thermal lesion.

Figure 3C:
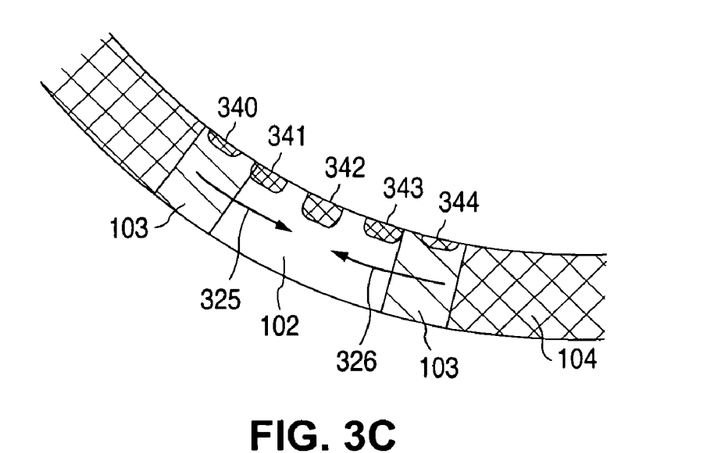

FIG. 3C illustrates an alternative embodiment that combines the methods illustrated in FIGS. 3A and 3B. Thermal lesions 340, 341, 342, 343, and 344 of varied size are created across ischemic region 102 and are also created in the area 103 adjacent the ischemic region.

To make the multiple thermal lesions illustrated in FIGS. 3A-3C with a catheter 110 having a single transducer element 115, as illustrated in FIG. 2B, transducer 115 is repositioned each time a new thermal lesion is to be created. However, if multiple thermal lesions are to be created, single transducer 115 must be repositioned several times, which can make the procedure lengthy and may expose the patient to additional risk of complications.

Figure 4:
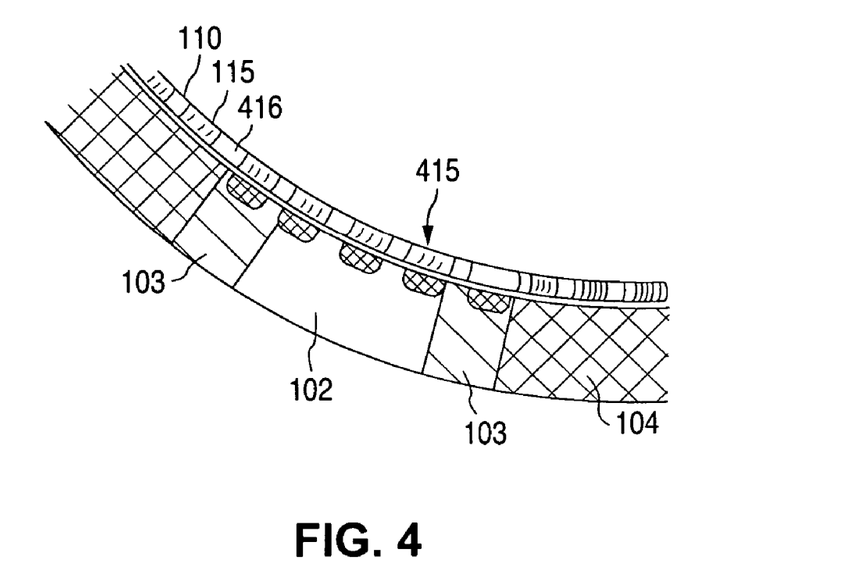
FIG. 4 illustrates a catheter having an array of ultrasound transducers positioned over the ischemic region and the multiple lesions produced by the ultrasound energy from transducers in the array.

An alternative apparatus that avoids or reduces the need to reposition transducer 115 several times is illustrated in FIG. 4. An array 415 of transducers 115 is provided at the distal end of catheter 110. While ten transducers 115 are shown in array 415 of FIG. 4, the number of transducers may be more or less, and catheter 110 typically contains an array of between 5 and 15 ultrasound transducers 115 depending on the application. The spacing 416 between each transducer 115 can also vary with the application. For example, in one treatment regime, a thermal lesion is created for every one square centimeter of surface area of ischemic region 102 on the endocardium or epicardium. To treat an ischemic region 102 that has 25 cm$^2$ surface area and that is approximately square (5 cm×5 cm), a catheter 110 should have an array 415 of at least 5 transducers with, for instance, one transducer per cm in the array (e.g., transducers of 4 mm in length with a spacing 416 of 6 mm between them). To cover the 25 cm$^2$ ischemic area, such an array can be positioned five times to create five lines of five thermal lesions for a total of 25 thermal lesions. With respect to the spacing 416, small, tightly spaced ultrasound transducers can be used to make small, tightly spaced thermal lesions, but may make distal end 117 of catheter 110 less flexible.

The transducer array 415 only needs to be positioned so that a portion of the transducers 115 overlies ischemic region 102. Radiopaque or other markers on the catheter can be used to identify which of the transducers 115 are located over the ischemic region 102 and adjacent region 103. The identified transducers can be selectively activated by the controller to produce thermal lesions in region 102 and, if desired, region 103. The controller can also individually control the power output (by controlling the voltage, duty cycle, and/or frequency) of each transducer, to produce thermal lesions of varying sizes. Typically catheter 110 having an array 415 of transducers 115 will not need to be repositioned, or will only need to be repositioned a relatively small number of times, to create the desired pattern of thermal lesions across the entire ischemic region 102. The size of ischemic region 102 typically will be a factor in determining whether any repositioning of array 415 will be necessary.

Figure 5:
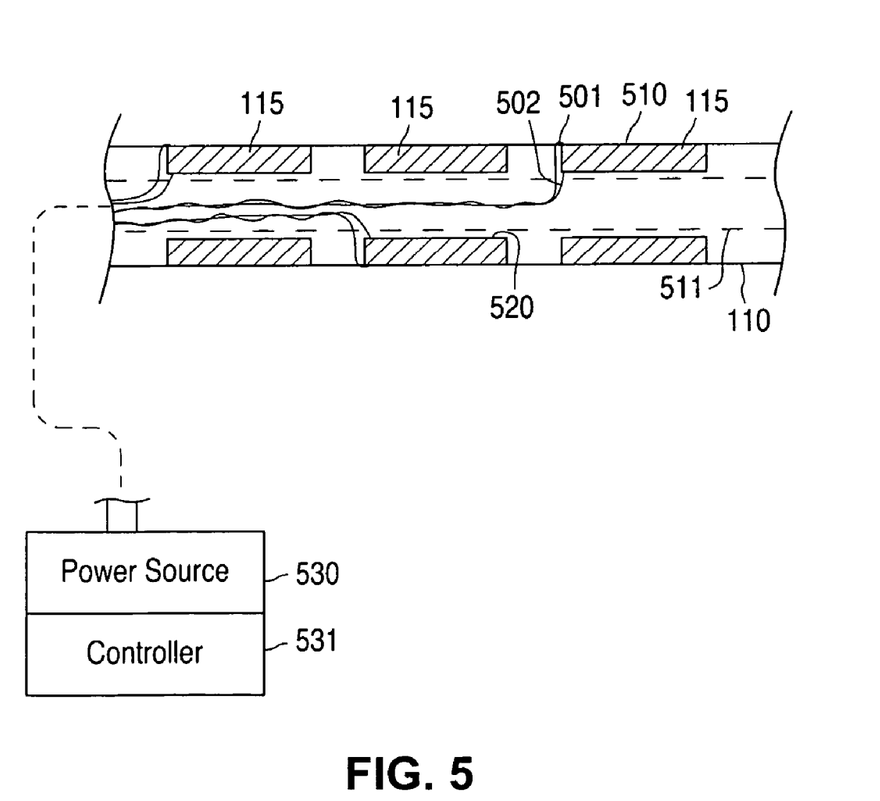
FIG. 5 is a sectional representation of a portion of the array of transducers illustrated in FIG. 4 and the electrical leads connecting the transducers to the power source and controller.

Typically, each transducer 115 of multi-transducer catheter 110 is individually coupled to the power source. As illustrated in the embodiment of FIG. 5, each of the multiple transducers 115 has an electrical lead 501 connected to the outer surface 510 of the transducer and an electrical lead 502 connected to the inner surface 520 of the transducer. Electrical leads 501, 502 can be narrow (44-48 gauge) coaxial cable or twisted pair balanced feed line. The coaxial cable contains an inner wire for carrying the electrical signal, and a ground wire surrounding the inner wire to shield the inner wire from electrical noise. Coaxial cables or twisted pair balanced feed lines are typically used for electrical leads 501, 502 instead of bare wire to minimize impedance loss over the length of the wire due to standing wave reflections. Electrical leads 501, 502 run through an inner lumen 511 of catheter 110 to the power source, and are flexible, so as not to hinder plasticity of catheter 110. Inner lumen 511 will also contain components (not shown) for steering and guiding catheter 110 through the body.

Electrical leads 501, 502 deliver energy to the transducers 115 from a power source 530. Controller 531 controls power source 530. The controller 531 (typically containing a microprocessor) can be programmed to selectively turn on and individually control each transducer 115. Transducers 115 can be activated simultaneously or sequentially, and power can be controlled to each using the amplitude of the voltage, duty cycle, or frequency as described above.

B. Creating Thermal Lesions Located Internal to the Myocardium

Figure 6:
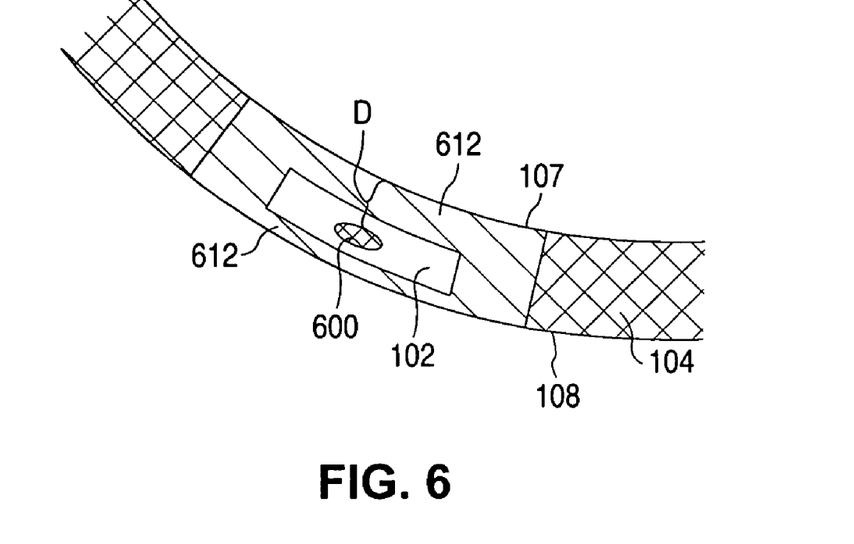
FIG. 6 is a sectional representation of an internal ischemic region that is located within the myocardium and a thermal lesion centered in the ischemic region. The lesion does not contact the endocardium or epicardium.

A method of treatment within the present invention uses ultrasonic energy having a frequency at or above 1 MHz to create thermal lesion(s) that are internal to the myocardium and advantageously do not damage the endocardium or epicardium. FIG. 6 illustrates an embodiment of this method, where a thermal lesion 600 has been created at a depth D within the myocardium 104. Thermal lesion 600 does not overlap the endocardium 107 or the epicardium 108. Likewise, thermal lesion 600 does not overlap healthy myocardium 612 between the endocardium 107 or epicardium 108 and the ischemic region 102.

Figure 7:
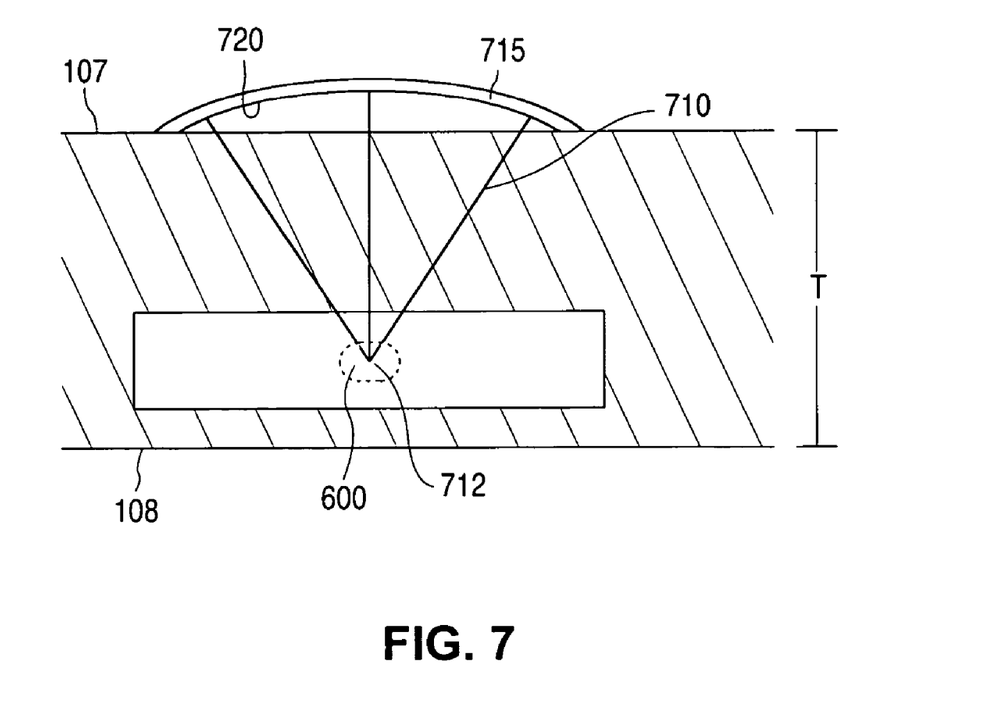
FIG. 7 is a sectional representation of a concave ultrasound transducer element located on the myocardium of FIG. 6, where ultrasound energy delivered from the concave transducer element is focused into the ischemic region.

FIG. 7 illustrates a curved ultrasonic transducer 715 for creating thermal lesion 600 of FIG. 6. Transducer 715 is similar to transducer 115, except that transducer 715 is shaped so that ultrasonic energy 710 radiates from the concave surface 720 and converges at a site 712 beyond the transducer. Transducer 715 can be positioned over ischemic region 102 and set on the endocardial 107 (or epicardial 108) surface of myocardium 104 with the concave surface 720 facing the myocardium. Ultrasound energy emitted from transducer 715 will be focused in the ischemic region to form thermal lesion 600.

Figure 8A:
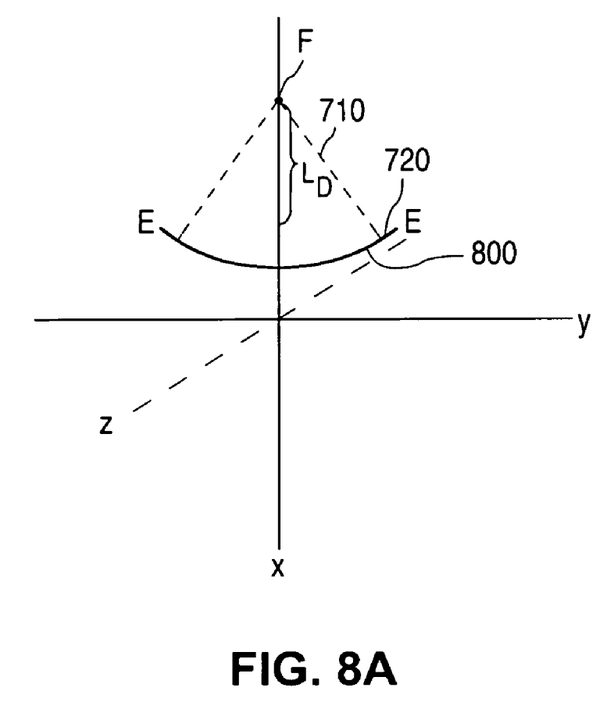
FIGS. 8A and 8B illustrate exemplary curves that the transducer illustrated in FIG. 7 may be shaped as to focus the ultrasound energy.
Figure 8B:
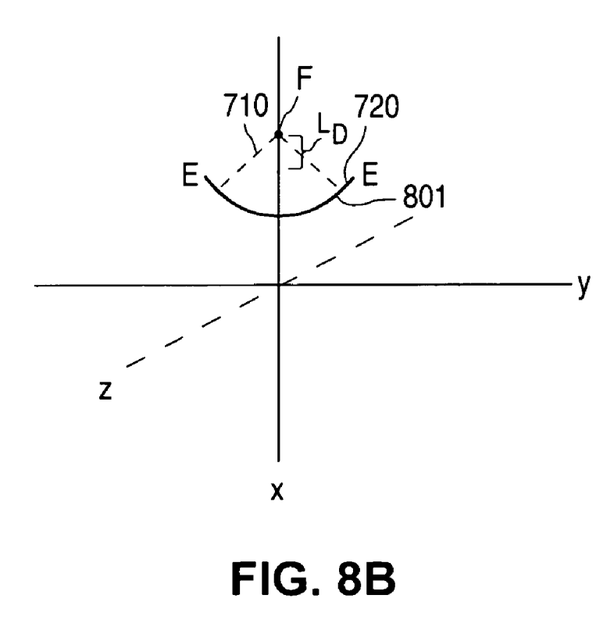

Transducer 715 can have, for instance, a spherical curve, as illustrated in FIG. 8A by exemplary curve 800, a parabolic curve, as illustrated by exemplary curve 801 of FIG. 8B, or any other shape that focuses the ultrasound energy. For transducer 715 having a given shape, such as curve 800, ultrasonic energy 710 will radiate from the concave side 720 of the curve and converge at a focal site F. The depth D that thermal lesion 600 is created within myocardium 104 is determined by the length $L_D$ that focal site F extends beyond the ends E of the curve. Length $L_D$ is determined by the degree of curvature and arc length of the curve. Healthy myocardium has a thickness, T, (shown in FIG. 7) of approximately 1-2 mm, but the myocardium of diseased hearts can be thicker, for instance up to approximately 7 mm. Therefore, the depth D of thermal lesion 600 can be set to between, for example, 1 and 7 mm.

Figure 9A:
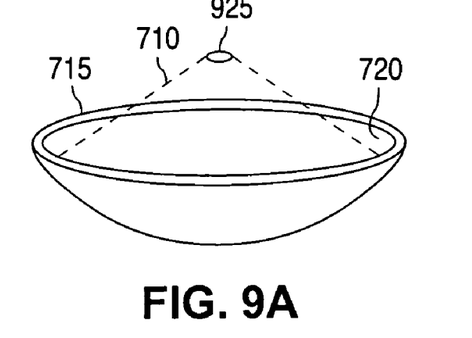
FIGS. 9A, 9B, and 9C illustrate exemplary ultrasound transducers shaped to focus ultrasound energy.
Figure 9B:
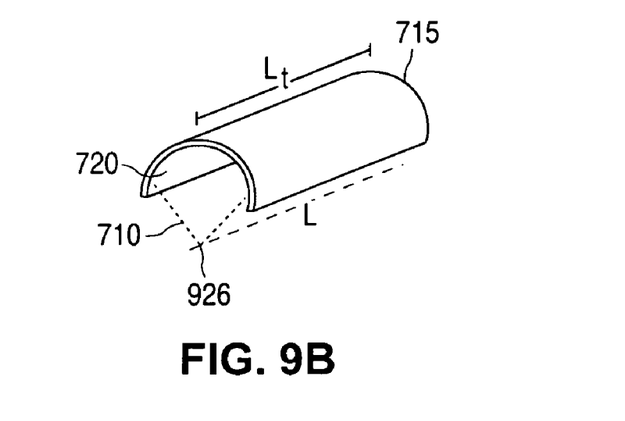
Figure 9C:
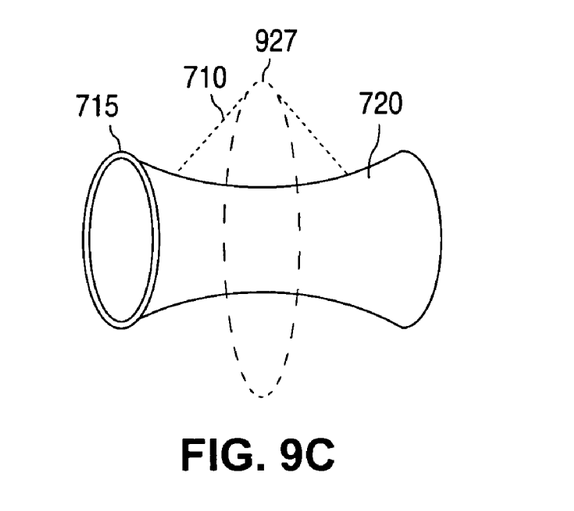

Curved transducer 715 can have a variety of shapes, including, but not limited to, the exemplary shapes illustrated in FIGS. 9A, 9B, and 9C. FIG. 9A illustrates transducer 715 in an exemplary bowl-like shape formed by the surface of rotation of a curve, such as curve 800 or 801, about the x-axis in FIGS. 8A and 8B, respectively. Ultrasonic energy 710 radiating from a transducer 715 of FIG. 9A converges in a central site, for example, site 925.

FIG. 9B illustrates transducer 715 having an exemplary shape that is a partial cylinder formed by the surface of translation of a curve, such as curve 800 or 801, along the z-axis of FIGS. 8A and 8B, respectively. Ultrasonic energy 710 emanating from transducer 715 of FIG. 9B converges along line 926, having a length L approximately equal to the length $L_t$ of the transducer.

FIG. 9C illustrates transducer 715 having an exemplary hollow tubular shape with flared ends, such as a hyperboloid-like shape, formed by the surface of rotation of the curve, such as curve 800 or 801, about the y-axis in FIGS. 8A and 8B, respectively. Ultrasonic energy 710 radiating from transducer 715 of FIG. 9C converges along a circle 927 surrounding the transducer. Therefore, ultrasound energy emitted from a hyperboloid-like shaped transducer 715 will form a thermal lesion in the form of an arc through the tissue, damaging the endocardial (or epicardial) surface at the point where the circle 927 intersects the endocardial (or epicardial) surface. However, a hyperboloid-like shaped transducer advantageously does not have to be oriented in a particular direction to irradiate ultrasound energy into the tissue.

Shaped transducer 715 can be formed by cutting, typically with an ultrasonic or mechanical machining process, sintering a powder of, or molding the ceramic material into the desired shape. The shaped ceramic is then polarized in a known process, for example exposing the ceramic to a high electric field, so that it will radiate ultrasound energy. Transducer 715 can be formed from, for example, LTZ2 (Staveley Sensors, Inc., East Hartford, Conn.), PZT, or other lead-ceramic materials, such as $PbTiO_3$ (lead titanate) or $PbZrO_3$ (lead zirconate).

The resonant frequency of the transducer is inversely proportional to the thickness of the ceramic material. Typically the ceramic material is between 0.006 inch (0.15 mm) to 0.015 inch (0.38 mm) thick, depending on the desired resonant frequency. The longest dimension of transducer 715 is typically between 1 and 10 mm.

Figure 10:
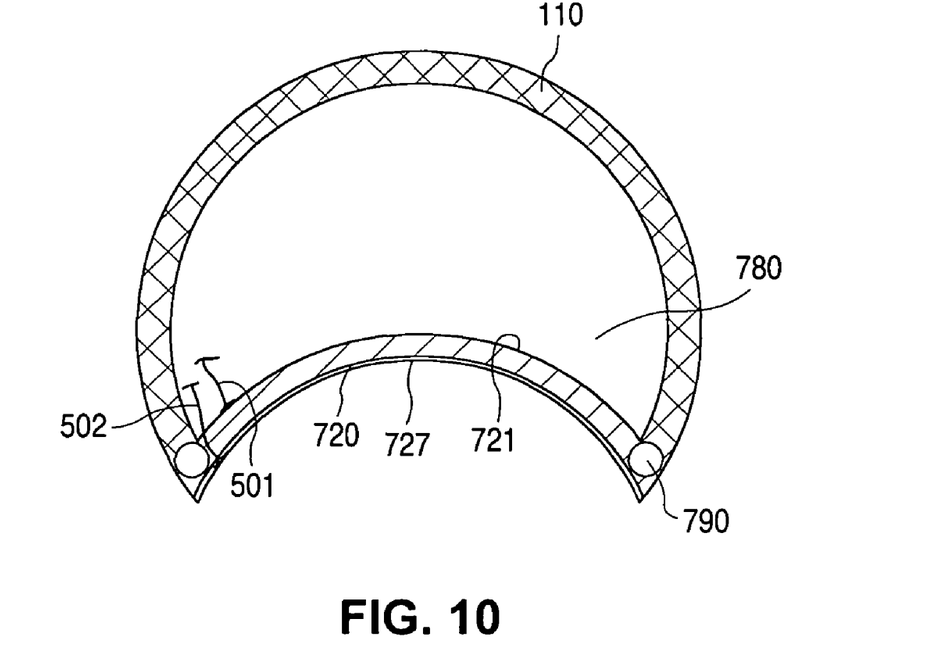
FIG. 10 is a sectional end-on view of a concave ultrasound transducer mounted in a catheter.

FIG. 10 illustrates a sectional view of concave transducer 715 mounted in catheter 110. The front 720 and back 721 surfaces of the transducer 715 are typically coated with conductive material plating (not shown), such as gold, platinum or palladium, or other similar conductive materials. A thin layer of a bio-compatible coating 727, such as Epo-Tek 353 ND (Epo-Tek, Inc., Billerica, Mass.) or parylene is typically applied to concave surface 720. Coating 727 protects and strengthens the transducer, electrically isolates the conductive surfaces, and can be used to match impedance between the crystal and the tissue.

The transducer 715 is mounted to the catheter 110 through an o-ring 790, or other mechanical means that seals transducer 715 to catheter 110. Solder joints are used to mechanically attach and electrically connect the electrical leads 501, 502 to the transducer 715. In addition to solder joints, a conductive epoxy, cold solders, ultrasonic welds and other similar attachment techniques can be used. Electrical leads 501, 502 are generally connected at the edge of transducer 715 because solder may dampen the vibrations of the transducer.

There is a gap 780 between transducer 715 and catheter 110. Gap 780 may contain any suitable low-density material, including gaseous substances such as ambient air, oxygen, nitrogen, helium, an open-cell polymeric foam, a closed cell polymeric foam, and other similar polymeric materials and mixtures thereof. Ultrasonic energy does not travel through low-density material but instead is reflected by the low-density materials. Therefore, the ultrasonic energy that radiates inward from transducer 715, off back surface 721, is reflected rather than being absorbed by the catheter. Gap 780 can be extremely thin, for example, 1/1000 of an inch (0.025 mm), to leave room within catheter 110 for electrical leads 501, 502 and additional steering and guiding components (not shown). Catheter 110 is typically between 5 and 8 french in diameter.

Because the ultrasonic energy emitted from transducer 715 is focused, less power, for example, 2-3 Watts, is typically needed to create the thermal lesion 600 than to create a thermal lesion from an unfocused transducer. The duration of application of the ultrasonic energy will be similar to those listed above.

Figure 11:
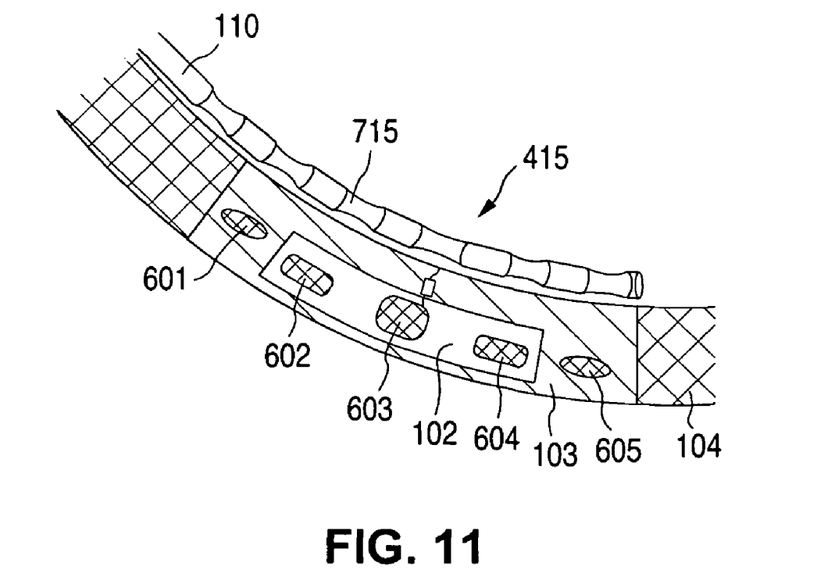
FIG. 11 illustrates a catheter having multiple concave transducer elements and lesions produced in an internal ischemic region and adjacent myocardium by the ultrasound energy delivered by the transducers.

FIG. 11 illustrates a catheter 110 having an array 415 of curved transducers 715 at a distal end. Curved transducers 715, illustrated here as having the exemplary hyperboloid-like shape illustrated in FIG. 9C, focuses ultrasonic energy as described above. The transducers 715 in array 415 are connected to a power source and controller as illustrated in FIG. 5 and operate in the same manner as described above with respect to FIG. 5.

In FIG. 11, multiple thermal lesions 601, 602, 603, 604, 605 have been created at a depth D within myocardium 104 by transducers 715 in array 415. The thermal lesions have a gradient of sizes, as described above with respect to FIG. 3B, and lesions 601 and 605 have been created within the healthier tissue of region 103, as describe above in reference to FIG. 3A.

While particular embodiments of the present invention have been shown and described, it will be clear to those of ordinary skill in the art that changes and modifications can be made without departing from this invention in its broader aspects and, therefore, the appended claims are to encompass all such changes and modifications as falling within the scope of this invention.

What is claimed is:

1. An apparatus for stimulating angiogenesis in a biological tissue, comprising:
   a catheter including a distal portion configured to be inserted into a body lumen of a patient;
   a tissue stimulating element at the distal portion of the catheter, the tissue stimulating element configured to radiate ultrasonic energy at a power that causes cellular damage to biological tissue and subsequent production of an angiogenesis stimulating substance;
   a power source that provides electrical energy to the tissue stimulating element; and
   a controller configured to control the temperature of the tissue stimulating element to a temperature at or below about 80 deg. C.,
   wherein the tissue stimulating element is configured to radiate the ultrasonic energy through a surface of the biological tissue to a region below the surface of the biological tissue at which the ultrasonic energy causes the cellular damage without causing substantial damage to the surface directly above the cellular damage.

2. The apparatus of claim 1, further comprising a temperature sensor disposed on the distal portion of the catheter, wherein the temperature sensor is in communication with the controller to provide feedback to the controller.

3. The apparatus of claim 1, wherein the tissue stimulating element includes an ultrasonic transducer.

4. The apparatus of claim 3, wherein the ultrasonic transducer is configured to operate at a frequency at or above 1 MHz.

5. The apparatus of claim 3, wherein the ultrasonic transducer is configured to operate at a frequency between 1 MHz and 15 MHz.

6. The apparatus of claim 3, wherein the ultrasonic transducer is configured to operate at a frequency between 4 MHz and 10 MHz.

7. The apparatus of claim 1, wherein the tissue stimulating element includes a side-fire ultrasonic transducer.

8. The apparatus of claim 1, wherein the tissue stimulating element is configured to not cut or pierce the biological tissue with the radiated ultrasonic energy that causes the cellular damage below the surface of the biological tissue.

9. The apparatus of claim 1, wherein the tissue stimulating element is configured to radiate the ultrasonic energy from outside a myocardium of a heart, the ultrasonic energy being focused by the tissue stimulating element to create a thermal lesion internal to the myocardium without damaging any of the endocardium and epicardium of the heart.

10. The apparatus of claim 1, wherein the tissue stimulating element includes a curved surface from which the ultrasonic energy is radiated, the curved surface having a curvature and an arc length that causes the ultrasonic energy to converge at a distance beyond the curved surface.

11. The apparatus of claim 1, wherein the tissue stimulating element includes a transducer having a front surface and a back surface, the front surface being concave, the back surface being convex, and wherein the apparatus further comprises a gap existing between the back surface and a side of the catheter, at least a portion of the gap enclosed by the transducer and the side of the catheter.

12. The apparatus of claim 11, additionally including a low-density material in the gap, the low-density material being any of ambient air, oxygen gas, nitrogen gas, helium gas, an open-cell polymeric foam, a closed cell polymeric foam, or mixtures thereof.

13. The apparatus of claim 1, wherein the ultrasonic energy itself induces molecular motion sufficient to heat the biological tissue and cause the cellular damage.

14. The apparatus of claim 1, wherein the tissue stimulating element is configured to generate the ultrasonic energy at a power between about 2 watts and about 3 watts to cause the cellular damage in the form of a thermal lesion below the surface of the biological tissue.

15. An apparatus for stimulating angiogenesis in a biological tissue, comprising:
a catheter including a distal portion configured to be inserted into a body lumen of a patient;
a tissue stimulating element at the distal portion of the catheter, the tissue stimulating element configured to radiate ultrasonic energy at a power that causes cellular damage to biological tissue and subsequent production of an angiogenesis stimulating substance;
a power source that provides electrical energy to the tissue stimulating element; and
a controller configured to control the temperature of the tissue stimulating element to a temperature at or below about 80 deg. C.,
wherein the tissue stimulating element includes an array of tissue stimulating devices positioned adjacent to each other, wherein each of the tissue stimulating devices are independently coupled to the power source and are selectively controlled by the controller.

16. The apparatus of claim 15, wherein the tissue stimulating element is configured to produce the ultrasonic energy at a power that causes a thermal lesion in the biological tissue.

17. The apparatus of claim 15, wherein the array of tissue stimulating devices are configured to simultaneously produce multiple thermal lesions of different sizes in the biological tissue.

18. An apparatus for stimulating angiogenesis in a biological tissue, comprising:
a catheter configured to be inserted into a body lumen of a patient;
a tissue stimulating element located at a distal portion of the catheter for causing the production of an angiogenesis stimulating substance;
a power source that provides energy to the tissue stimulating element; and
a controller configured to control the temperature of the tissue stimulating element to a temperature at or below about 80 deg. C.,
wherein the tissue stimulating element is adapted to not form a channel in the tissue for the production of the angiogenesis stimulating substance, and wherein the tissue stimulating element includes an array of tissue stimulating devices positioned adjacent to each other and wherein each of the tissue stimulating devices is configured to be activated or controlled independently of one another.

19. The apparatus of claim 18, wherein the tissue stimulating element is configured to generate ultrasonic energy at a power that causes thermal cellular damage.

20. An apparatus for creating a thermal lesion in a biological tissue, comprising:
a catheter configured to be inserted into a body lumen of a patient;
a tissue stimulating element at a distal portion of the catheter, the tissue stimulating element configured to radiate energy, the tissue stimulating element having a shape that focuses the radiated energy to a focus region spaced apart from the tissue stimulating element such that when the tissue stimulating element is outside of a biological tissue, the radiated energy creates a thermal lesion at the focus region within the biological tissue without any thermal damage or any significant thermal damage to a surface of the biological tissue directly above the thermal lesion; and
a power source that provides energy to the tissue stimulating element.

21. The apparatus of claim 20, wherein the tissue stimulating element is configured to radiate the energy across the surface of the biological tissue to the focus region, the radiated energy being focused by the tissue stimulating element to create the thermal lesion at the focus region within the biological tissue without cutting or piercing the surface of the biological tissue.

22. The apparatus of claim 20, wherein the shape of the tissue stimulating element focuses the radiated energy to a line spaced apart from the tissue stimulating element.

23. The apparatus of claim 20, wherein the shape of the tissue stimulating element focuses the radiated energy to a circle spaced apart from the tissue stimulating element.

* * * * *